United States Patent
He et al.

(10) Patent No.: US 6,495,519 B1
(45) Date of Patent: Dec. 17, 2002

(54) INTERLEUKIN-1 β CONVERTING ENZYME LIKE APOPTOSIS PROTEASE-3 AND 4

(75) Inventors: Wei Wu He, Columbia; Craig A. Rosen, Laytonsville; Peter L. Hudson, Germantown; Gregg A. Hastings, Rockville, all of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/124,934

(22) Filed: Jul. 28, 1998

Related U.S. Application Data

(62) Division of application No. 08/334,251, filed on Nov. 1, 1994.

(51) Int. Cl.[7] .................. A61K 38/48; A61K 38/17; C12N 9/64; C07K 14/47
(52) U.S. Cl. .................. 514/12; 435/226; 435/219; 424/94.63; 424/94.65; 530/350
(58) Field of Search ................. 530/350; 424/94.65, 424/94.63; 435/226, 219; 514/12

(56) References Cited

U.S. PATENT DOCUMENTS 5,552,536 A  9/1996 Nicholson et al. ......... 536/23.1

FOREIGN PATENT DOCUMENTS

| CA | 2075662 | 2/1993 |
| EP | 533 226 | 3/1993 |
| WO | WO96/33268 | 10/1996 |

OTHER PUBLICATIONS

Callard et al. Cytokine Facts Book. New York: Academic Press, p. 31, 1994.*
GeneSeq Accession No: T66992 (Aug. 5, 1997).
GeneSeq Accession No.: T66970 (Jul. 21, 1997).
GeneSeq Accession No: T66993 (Aug. 5, 1997).
GeneSeq Accession No: W15247 (Jul. 21, 1997).
GeneSeq Accession No: W15262 (Aug. 5, 1997).
GeneSeq Accession No: W15263 (Aug. 5, 1997).
GenBank Accession No: U39613 (Jan. 19, 1996).
GenBank Accession No: U37448 (Dec. 14, 1995).
GenBank Accession No: U40281 (Jan. 27, 1996).
GenBank Accession No: U67319 (Mar. 19, 1997).
GenBank Accession No: U67320 (Mar. 19, 1997).
GenBank Accession No: U37449 (Dec. 14, 1995).
GenBank Accession No: H91868 (Nov. 29, 1995).
GeneSeq Accession No: V05471 (Jul. 2, 1998).
GeneSeq Accession No: T33567 (Dec. 6, 1996).
GeneSeq Accession No: V32608 (Oct. 26, 1998).
GeneSeq Accession No: V32615 (Oct. 26, 1998).
GeneSeq Accession No: W00677 (Dec. 6, 1996).
GeneSeq Accession No: W00372 (Jun. 26, 1997).
GeneSeq Accession No: W41688 (Jul. 2, 1998).
GeneSeq Accession No: W16600 (Jun. 26, 1997).
GeneSeq Accession No: W48945 (Oct. 26, 1998).
GeneSeq Accession No: W48937 (Oct. 26, 1998).
GenBank Accession No: U26943 (Aug. 29, 1995).
GenBank Accession No: U13737 (Apr. 14, 1995).
GenBank Accession No: U13738 (Apr. 14, 1995).
GenBank Accession No: T10341 (Jun. 7, 1994).
GenBank Accession No: H29199 (Jul. 17, 1995).
GenBank Accession No: N85243 (Apr. 1, 1996).
Cerretti et al., Science, vol. 256:97–100 (1992).
Walker et al., Cell, vol. 78:343–352 (1994).
Wang et al., Cell, vol. 78:739–750(1994).
Henkart, Immunity, vol. 4:195–201 (1996).
Kamens et al., The J. of Biol. Chem., vol. 270:15250–15256 (1995).
Munday et al., The J. of Biol. Chem., vol. 270:15870–15876 (1995).
Tewari et al., Cell, vol. 81:801–809 (1995).
Faucheu et al., EMBO Journal, vol. 14:1914–1922 (1995).
Greenfeder et al., The J. of Biol. Chem., vol. 270:13757–13765 (1995).
Miura et al., Cell, vol. 75:653–660 (1993).
Fernandes–Alnemri et al., The J. of Biol. Chem., vol. 269:30761–30764 (1994).
Ellis et al., Annu. Rev. Cell Biol., vol. 7:663–98 (1991).
Barinaga, Sciences, vol. 263:754–756 (1994).

\* cited by examiner

Primary Examiner—Christopher S. F. Low
Assistant Examiner—Gabriele E. Bugalsky
(74) Attorney, Agent, or Firm—Human Genome Sciences, Inc.

(57) ABSTRACT

Disclosed are human interleukin-1 β converting enzyme like apoptosis proteases-3 and 4 and DNA (RNA) encoding such polypeptides. Also provided is a procedure for producing such polypeptides by recombinant techniques and antibodies and antagonists against such polypeptides. Also provided are methods of using the polypeptides, for example, as an antitumor agent, and antiviral agent, and antibodies and antagonists against such polypeptides for example, for treating Alzheimer's disease, Parkinson's disease, rheumatoid arthritis and head injury.

15 Claims, 7 Drawing Sheets

FIGURE 1A

```
  1  GCACGAGAAACTTTGCTGTGCGCGTTCTCCCGCGCGCGGGCTCAACTTTGTAGAGCGAGG   60

61  GGCCAACTTGGCAGAGCGCGCGGCCAGCTTTGCAGAGAGCGCCCTCCAGGGACTATGCGT  120

121  GCGGGGACACGGGTCGCTTTGGGCTCTTCCACCCCTGCGGAGCGCACTACCCCGAGCCAG  180

181  GGGCGGTGCAAGCCCCGCCCGGCCCTACCCAGGGCGGCTCCTCCCTCCGCAGCGCCGAGA  240

241  CTTTTAGTTTCGCTTTCGCTAAAGGGGCCCCAGACCCTTGCTGCGGAGCGACGGAGAGAG  300

301  ACTGTGCCAGTCCCAGCCGCCCTACCGCCGTGGGAACGATGGCAGATGATCAGGGCTGTA  360
  1                                             M  A  D  D  Q  G  C  I    8

361  TTGAAGAGCAGGGGGTTGAGGATTCAGCAAATGAAGATTCAGTGGATGCTAAGCCAGACC  420
  9   E  E  Q  G  V  E  D  S  A  N  E  D  S  V  D  A  K  P  D  R   28

421  GGTCCTCGTTTGTACCGTCCCTCTTCAGTAAGAAGAAGAAAAATGTCACCATGCGATCCA  480
 29   S  S  F  V  P  S  L  F  S  K  K  K  K  N  V  T  M  R  S  I   48

481  TCAAGACCACCCGGGACCGAGTGCCTACATATCAGTACAACATGAATTTTGAAAAGCTGG  540
 49   K  T  T  R  D  R  V  P  T  Y  Q  Y  N  M  N  F  E  K  L  G   68

541  GCAAATGCATCATAATAAACAACAAGAACTTTGATAAAGTGACAGGTATGGGCGTTCGAA  600
 69   K  C  I  I  I  N  N  K  N  F  D  K  V  T  G  M  G  V  R  N   88

601  ACGGAACAGACAAAGATGCCGAGGCGCTCTTCAAGTGCTTCCGAAGCCTGGGTTTTGACG  660
 89   G  T  D  K  D  A  E  A  L  F  K  C  F  R  S  L  G  F  D  V  108

661  TGATTGTCTATAATGACTGCTCTTGTGCCAAGATGCAAGATCTGCTTAAAAAAGCTTCTG  720
109   I  V  Y  N  D  C  S  C  A  K  M  Q  D  L  L  K  K  A  S  E  128

721  AAGAGGACCATACAAATGCCGCCTGCTTCGCCTGCATCCTCTTAAGCCATGGAGAAGAAA  780
129   E  D  H  T  N  A  A  C  F  A  C  I  L  L  S  H  G  E  E  N  148

781  ATGTAATTTATGGGAAAGATGGTGTCACACCAATAAAGGATTTGACAGCCCACTTTAGGG  840
149   V  I  Y  G  K  D  G  V  T  P  I  K  D  L  T  A  H  F  R  G  168

841  GGGATAGATGCAAAACCCTTTTAGAGAAACCCAAACTCTTCTTCATTCAGGCTTGCCGAG  900
169   D  R  C  K  T  L  L  E  K  P  K  L  F  F  I  Q  A  C  R  G  188

901  GGACCGAGCTTGATGATGCCATCCAGGCCGACTCGGGGCCCATCAATGACACAGATGCTA  960
189   T  E  L  D  D  A  I  Q  A  D  S  G  P  I  N  D  T  D  A  N  208
```

FIGURE 1B

```
 961  ATCCTCGATACAAGATCCCAGTGGAAGCTGACTTCCTCTTCGCCTATTCCACGGTTCCAG  1020
 209    P  R  Y  K  I  P  V  E  A  D  F  L  F  A  Y  S  T  V  P  G   228

1021  GCTATTACTCGTGGAGGAGCCCAGGAAGAGGCTCCTGGTTTGTGCAAGCCCTCTGCTCCA  1080
 229    Y  Y  S  W  R  S  P  G  R  G  S  W  F  V  Q  A  L  C  S  I   248

1081  TCCTGGAGGAGCACGGAAAAGACCTGGAAATCATGCAGATCCTCACCAGGGTGAATGACA  1140
 249    L  E  E  H  G  K  D  L  E  I  M  Q  I  L  T  R  V  N  D  R   268

1141  GAGTTGCCAGGCACTTTGAGTCTCAGTCTGATGACCCACACTTCCATGAGAAGAAGCAGA  1200
 269    V  A  R  H  F  E  S  Q  S  D  D  P  H  F  H  E  K  K  Q  I   288

1201  TCCCCTGTGTGGTCTCCATGCTCACCAAGGAACTCTACTTCAGTCAATAGCCATATCAGG  1260
 289    P  C  V  V  S  M  L  T  K  E  L  Y  F  S  Q                  303

1261  GGTACATTCTAGCTGAGAAGCAATGGGTCACTCATTAATGAATCACATTTTTTTATGCTC  1320

1321  TTGAAATATTCAGAAATTCTCCAGGATTTTAATTTCAGGAAAATGTATT  1369
```

FIGURE 2A

```
  1 GCACGAGCGGATGGGTGCTATTGTGAGGCGGTTGTAGAAGAGTTTCGTGAGTGCTCGCAG  60

61 CTCATACCTGTGGCTGTGTATCCGTGGCCACAGCTGGTTGGCGTCGCCTTGAAATCCCAG 120

121 GCCGTGAGGAGTTAGCGAGCCCTGCTCACACTCGGCGCTCTGGTTTTCGGTGGGTGTGCC 180

181 CTGCACCTGCCTCTTCCCGCATTCTCATTAATAAAGGTATCCATGGAGAACACTGAAAAC 240
  1                                                  M  E  N  T  E  N   6

241 TCAGTGGATTCAAAATCCATTAAAAATTTGGAACCAAAGATCATACATGGAAGCGAATCA 300
  7  S  V  D  S  K  S  I  K  N  L  E  P  K  I  I  H  G  S  E  S  26

301 ATGGACTCTGGAATATCCCTGGACAACAGTTATAAAATGGATTATCCTGAGATGGGTTTA 360
 27  M  D  S  G  I  S  L  D  N  S  Y  K  M  D  Y  P  E  M  G  L  46

361 TGTATAATAATTAATAATAAGAATTTTCATAAAAGCACTGGAATGACATCTCGGTCTGGT 420
 47  C  I  I  I  N  N  K  N  F  H  K  S  T  G  M  T  S  R  S  G  66

421 ACAGATGTCGATGCAGCAAACCTCAGGGAAACATTCAGAAACTTGAAATATGAAGTCAGG 480
 67  T  D  V  D  A  A  N  L  R  E  T  F  R  N  L  K  Y  E  V  R  86

481 AATAAAAATGATCTTACACGTGAAGAAATTGTGGAATTGATGCGTGATGTTTCTAAAGAA 540
 87  N  K  N  D  L  T  R  E  E  I  V  E  L  M  R  D  V  S  K  E  106

541 GATCACAGCAAAAGGAGCAGTTTTGTTTGTGTGCTTCTGAGCCATGGTGAAGAAGGAATA 600
107  D  H  S  K  R  S  S  F  V  C  V  L  L  S  H  G  E  E  G  I  126

601 ATTTTTGGAACAAATGGACCTGTTGACCTGAAAAAAATAACAAACTTTTTCAGAGGGGAT 660
127  I  F  G  T  N  G  P  V  D  L  K  K  I  T  N  F  F  R  G  D  146

661 CGTTGTAGAAGTCTAACTGGAAAACCCAAACTTTTCATTATTCAGGCCTGCCGTGGTACA 720
147  R  C  R  S  L  T  G  K  P  K  L  F  I  I  Q  A  C  R  G  T  166

721 GAACTGGACTGTGGCATTGAGACAGACAGTGGTGTTGATGATGACATGGCGTGTCATAAA 780
167  E  L  D  C  G  I  E  T  D  S  G  V  D  D  D  M  A  C  H  K  186

781 ATACCAGTGGAGGCCGACTTCTTGTATGCATACTCCACAGCACCTGGTTATTATTCTTGG 840
187  I  P  V  E  A  D  F  L  Y  A  Y  S  T  A  P  G  Y  Y  S  W  206
```

FIGURE 2B

```
 841 CGAAATTCAAAGGATGGCTCCTGGTTCATCCAGTCGCTTTGTGCCATGCTGAAACAGTAT  900
 207  R   N   S   K   D   G   S   W   F   I   Q   S   L   C   A   M   L   K   Q   Y   226

901 GCCGACAAGCTTGAATTTATGCACATTCTTACCCGGGTTAACCGAAAGGTGGCAACAGAA  960
 227  A   D   K   L   E   F   M   H   I   L   T   R   V   N   R   K   V   A   T   E   246

961 TTTGAGTCCTTTTCCTTTGACGCTACTTTTCATGCAAAGAAACAGATTCCATGTATTGTT 1020
 247  F   E   S   F   S   F   D   A   T   F   H   A   K   K   Q   I   P   C   I   V   266

1021 TCCATGCTCACAAAAGAACTCTATTTTTATCACTAAAGAAATGGTTGGTTGGTGGTTTTT 1080
 267  S   M   L   T   K   E   L   Y   F   Y   H   *                                       277

1081 TTTAGTTTGTATGCCAAGTGAGAAGATGGTATATTTGGGTACTGTATTTCCCTCTCATTG 1140

1141 GGGACCTACTCTCATGCTG 1159
```

FIGURE 3B

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1371 BASE PAIRS
      (B) TYPE: NUCLEIC ACID (C) STRANDEDNESS: SINGLE
            (D) TOPOLOGY: LINEAR (ii) MOLECULE TYPE: cDNA (xi) SEQUENCE DESCRIPTION: SEQ ID NO:1:

```
GCACGAGAAA CTTTGCTGTG CGCGTTCTCC CGCGCGCGGG CTCAACTTTG TAGAGCGAGG      60
GGCCAACTTG GCAGAGCGCG CGGCCAGCTT TGCAGAGAGC GCCCTCCAGG GACTATGCGT     120
GCGGGGACAC GGGTCGCTTT GGGCTCTTCC ACCCCTGCGG AGCGCACTAC CCCGAGCCAG     180
GGGCGGTGCA AGCCCCGCCC GGCCCTACCC AGGGCGGCTC CTCCCTCCGC AGCGCCGAGA     240
CTTTTAGTTT CGCTTTCGCT AAAGGGGCCC CAGACCCTTG CTGCGGAGCG ACGGAGAGAG     300
ACTGTGCCAG TCCCAGCCGC CCTACCGCCG TGGGAACGAT GGCAGATGAT TCAGGGCTGT     360
ATTGAAGAGC AGGGGGTTGA GGATTCAGCA AATGAAGATT CAGTGGATGC TAAGCCAGAC     420
CGGTCCTCGT TTGTACCGTC CCTCTTCAGT AAGAAGAAGA AAAATGTCAC CATGCGATCC     480
ATCAAGACCA CCCGGGACCG AGTGCCTACA TATCAGTACA ACATGAATTT TGAAAAGCTG     540
GGCAAATGCA TCATAATAAA CAACAAGAAC TTTGATAAAG TGACAGGTAT GGGCGTTCGA     600
AACGGAACAG ACAAAGATGC CGAGGCGCTC TTCAAGTGCT TCCGAAGCCT GGGTTTTGAC     660
GTGATTGTCT ATAATGACTG CTCTTGTGCC AAGATGCAAG ATCTGCTTAA AAAAGCTTCT     720
GAAGAGGACC ATACAAATGC CGCCTGCTTC GCCTGCATCC TCTTAAGCCA TGGAGAAGAA     780
AATGTAATTT ATGGGAAAGA TGGTGTCACA CCAATAAAGG ATTTGACAGC CCACTTTAGG     840
GGGGATAGAT GCAAAACCCT TTTAGAGAAA CCCAAACTCT TCTTCATTCA GGCTTGCCGA     900
GGGACCGAGC TTGATGATGG CATCCAGGCC GACTCGGGGC CATCAATGA CACAGATGCT     960
AATCCTCGAT ACAAGATCCC AGTGGAAGCT GACTTCCTCT TCGCCTATTC CACGGTTCCA    1020
GGCTATTACT CGTGGAGGAG CCCAGGAAGA GGCTCCTGGT TTGTGCAAGC CCTCTGCTCC    1080
ATCCTGGAGG AGCACGGAAA AGACCTGGAA ATCATGCAAA TCCTCCACCA GGGTGAATGA    1140
CAGAGTTGCC AGGCACTTTG AGTCTCAGTC TGATGACCCA CACTTCCATG AGAAGAAGCA    1200
GATCCCCTGT GTGGTCTCCA TGCTCACCAA GGAACTCTAC TTCAGTCAAT AGCCATATCA    1260
GGGGTACATT CTAGCTGAGA AGCAATGGGT CACTCATTAA TGAATCACAT TTTTTTATGC    1320
TCTTGAAATA TTCAGAAATT CTCCAGGATT TTAATTTCAG GAAAATGTAT T             1371
```

(2) INFORMATION FOR SEQ ID NO:2:

(i) SEQUENCE CHARACTERISTICS:
        (A) LENGTH: 341 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

Met Arg Ala Gly Thr Arg Val Ala Leu Gly Ser Ser Thr Pro Ala
                5                  10                  15

Glu Arg Thr Thr Pro Ser Gln Gly Arg Cys Lys Pro Arg Pro Ala
               20                  25                  30

Leu Pro Arg Ala Ala Pro Pro Ser Ala Ala Pro Arg Leu Leu Val
               35                  40                  45

Ser Leu Ser Leu Lys Gly Pro Gln Thr Leu Ala Ala Glu Arg Arg
               50                  55                  60

Arg Glu Thr Val Pro Val Pro Ala Ala Leu Pro Pro Trp Glu Arg

```
                     65                  70                  75
Thr Gln Met Ile Gln Gly Cys Ile Glu Glu Gln Gly Val Glu Asp
                 80                  85                  90
Ser Ala Asn Glu Asp Ser Val Asp Ala Lys Pro Asp Arg Ser Ser
                 95                 100                 105
Phe Val Pro Ser Leu Phe Ser Lys Lys Lys Asn Val Thr Met
                110                 115                 120
Arg Ser Ile Lys Thr Thr Arg Asp Arg Val Pro Thr Tyr Gln Tyr
                125                 130                 135
Asn Met Asn Phe Glu Lys Leu Gly Lys Cys Ile Ile Asn Asn
                140                 145                 150
Lys Asn Phe Asp Lys Val Thr Gly Met Gly Val Arg Asn Gly Thr
                155                 160                 165
Asp Lys Asp Ala Glu Ala Leu Phe Lys Cys Phe Arg Ser Leu Gly
                170                 175                 180
Phe Asp Val Ile Val Tyr Asn Asp Cys Ser Cys Ala Lys Met Gln
                185                 190                 195
Asp Leu Leu Lys Lys Ala Ser Glu Glu Asp His Thr Asn Ala Ala
                200                 205                 210
Cys Phe Ala Cys Ile Leu Leu Ser His Gly Glu Glu Asn Val Ile
                215                 220                 225
Tyr Gly Lys Asp Gly Val Thr Pro Ile Lys Asp Leu Thr Ala His
                230                 235                 240
Phe Arg Gly Asp Arg Cys Lys Thr Leu Leu Glu Lys Pro Lys Leu
                245                 250                 255
Phe Phe Ile Gln Ala Cys Arg Gly Thr Glu Leu Asp Asp Gly Ile
                260                 265                 270
Gln Ala Asp Ser Gly Pro Ile Asn Asp Thr Asp Ala Asn Pro Arg
                275                 280                 285
Tyr Lys Ile Pro Val Glu Ala Asp Phe Leu Phe Ala Tyr Ser Thr
                290                 295                 300
Val Pro Gly Tyr Tyr Ser Trp Arg Ser Pro Gly Arg Gly Ser Trp
                305                 310                 315
Phe Val Gln Ala Leu Cys Ser Ile Leu Glu Glu His Gly Lys Asp
                320                 325                 330
Leu Glu Ile Met Gln Ile Leu His Gln Gly Glu
                335                 340
```

(2) INFORMATION FOR SEQ ID NO:3:

(i) SEQUENCE CHARACTERISTICS:
        (A) LENGTH: 1159 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO:3:

```
GCACGAGCGG ATGGGTGCTA TTGTGAGGCG GTTGTAGAAG AGTTTCGTGA GTGCTCGCAG     60
CTCATACCTG TGGCTGTGTA TCCGTGGCCA CAGCTGGTTG GCGTCGCCTT GAAATCCCAG    120
GCCGTGAGGA GTTAGCGAGC CCTGCTCACA CTCGGCGCTC TGGTTTTCGG TGGGTGTGCC    180
CTGCACCTGC CTCTTCCCGC ATTCTCATTA ATAAAGGTAT CCATGGAGAA CACTGAAAAC    240
TCAGTGGATT CAAAATCCAT TAAAAATTTG GAACCAAAGA TCATACATGG AAGCGAATCA    300
```

-continued

```
ATGGACTCTG GAATATCCCT GGACAACAGT TATAAAATGG ATTATCCTGA GATGGGTTTA      360

TGTATAATAA TTAATAATAA GAATTTTCAT AAAAGCACTG GAATGACATC TCGGTCTGGT      420

ACAGATGTCG ATGCAGCAAA CCTCAGGGAA ACATTCAGAA ACTTGAAATA TGAAGTCAGG      480

AATAAAAATG ATCTTACACG TGAAGAAATT GTGGAATTGA TGCGTGATGT TTCTAAAGAA      540

GATCACAGCA AAAGGAGCAG TTTTGTTTGT GTGCTTCTGA GCCATGGTGA AGAAGGAATA      600

ATTTTTGGAA CAAATGGACC TGTTGACCTG AAAAAAATAA CAAACTTTTT CAGAGGGGAT      660

CGTTGTAGAA GTCTAACTGG AAAACCCAAA CTTTTCATTA TTCAGGCCTG CCGTGGTACA      720

GAACTGGACT GTGGCATTGA GACAGACAGT GGTGTTGATG ATGACATGGC GTGTCATAAA      780

ATACCAGTGG AGGCCGACTT CTTGTATGCA TACTCCACAG CACCTGGTTA TTATTCTTGG      840

CGAAATTCAA AGGATGGCTC CTGGTTCATC CAGTCGCTTT GTGCCATGCT GAAACAGTAT      900

GCCGACAAGC TTGAATTTAT GCACATTCTT ACCCGGGTTA ACCGAAAGGT GGCAACAGAA      960

TTTGAGTCCT TTTCCTTTGA CGCTACTTTT CATGCAAAGA AACAGATTCC ATGTATTGTT     1020

TCCATGCTCA CAAAAGAACT CTATTTTTAT CACTAAAGAA ATGGTTGGTT GGTGGTTTTT     1080

TTTAGTTTGT ATGCCAAGTG AGAAGATGGT ATATTTGGGT ACTGTATTTC CCTCTCATTG     1140

GGGACCTACT CTCATGCTG                                                  1159
```

(2) INFORMATION FOR SEQ ID NO:4:

(i) SEQUENCE CHARACTERISTICS:
        (A) LENGTH: 277 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:4:

```
Met Glu Asn Thr Glu Asn Ser Val Asp Ser Lys Ser Ile Lys Asn
                 5                  10                  15

Leu Glu Pro Lys Ile Ile His Gly Ser Glu Ser Met Asp Ser Gly
             20                  25                  30

Ile Ser Leu Asp Asn Ser Tyr Lys Met Asp Tyr Pro Glu Met Gly
             35                  40                  45

Leu Cys Ile Ile Ile Asn Asn Lys Asn Phe His Lys Ser Thr Gly
             50                  55                  60

Met Thr Ser Arg Ser Gly Thr Asp Val Asp Ala Ala Asn Leu Arg
             65                  70                  75

Glu Thr Phe Arg Asn Leu Lys Tyr Glu Val Arg Asn Lys Asn Asp
             80                  85                  90

Leu Thr Arg Glu Glu Ile Val Glu Leu Met Arg Asp Val Ser Lys
             95                 100                 105

Glu Asp His Ser Lys Arg Ser Ser Phe Val Cys Val Leu Leu Ser
            110                 115                 120

His Gly Glu Glu Gly Ile Ile Phe Gly Thr Asn Gly Pro Val Asp
            125                 130                 135

Leu Lys Lys Ile Thr Asn Phe Phe Arg Gly Asp Arg Cys Arg Ser
            140                 145                 150

Leu Thr Gly Lys Pro Lys Leu Phe Ile Ile Gln Ala Cys Arg Gly
            155                 160                 165

Thr Glu Leu Asp Cys Gly Ile Glu Thr Asp Ser Gly Val Asp Asp
            170                 175                 180
```

```
Asp Met Ala Cys His Lys Ile Pro Val Glu Ala Asp Phe Leu Tyr
                185                 190                 195

Ala Tyr Ser Thr Ala Pro Gly Tyr Tyr Ser Trp Arg Asn Ser Lys
                200                 205                 210

Asp Gly Ser Trp Phe Ile Gln Ser Leu Cys Ala Met Leu Lys Gln
                215                 220                 225

Tyr Ala Asp Lys Leu Glu Phe Met His Ile Leu Thr Arg Val Asn
                230                 235                 240

Arg Lys Val Ala Thr Glu Phe Glu Ser Phe Ser Phe Asp Ala Thr
                245                 250                 255

Phe His Ala Lys Lys Gln Ile Pro Cys Ile Val Ser Met Leu Thr
                260                 265                 270

Lys Glu Leu Tyr Phe Tyr His
                275
```

(2) INFORMATION FOR SEQ ID NO:5:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:5:

GATCGGATCC ATGCGTGCGG GGACACGGGT C                          31

(2) INFORMATION FOR SEQ ID NO:6:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:6:

GTACTCTAGA TCATTCACCC TGGTGGAGGA T                          31

(2) INFORMATION FOR SEQ ID NO:7:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:7:

GATCGGATCC ATGGAGAACA CTGAAAACTC A                          31

(2) INFORMATION FOR SEQ ID NO:8:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:8:

```
                                 -continued

GTACTCTAGA TTAGTGATAA AAATAGAGTT C                                 31

(2) INFORMATION FOR SEQ ID NO:9:

(i) SEQUENCE CHARACTERISTICS:
        (A) LENGTH:  22 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:9:

GACTATGCGT GCGGGGACAC GG                                           22

(2) INFORMATION FOR SEQ ID NO:10:

(i) SEQUENCE CHARACTERISTICS:
        (A) LENGTH:  53 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:10:

AATCAAGCGT AGTCTGGGAC GTCGTATGGG TATTCACCCT GGTGGAGGAT TTG          53

(2) INFORMATION FOR SEQ ID NO:11:

(i) SEQUENCE CHARACTERISTICS:
        (A) LENGTH:  21 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:11:

ACCATGGAGA ACACTGAAAA C                                            21

(2) INFORMATION FOR SEQ ID NO:12:

(i) SEQUENCE CHARACTERISTICS:
        (A) LENGTH:  53 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:12:

AATCAAGCGT AGTCTGGGAC GTCGTATGGG TAGTGATAAA AATAGAGTTC TTT          53
```

INTERLEUKIN-1 β CONVERTING ENZYME LIKE APOPTOSIS PROTEASE-3 AND 4

This application is entitled to the benefits of priority under 35 U.S.C. §120 for the subject matter disclosed in parent application U.S. Ser. No. 08/334,251, filed Nov. 1, 1994 still pending June 1997.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are interleukin-1 β converting enzyme like apoptosis protease-3 and interleukin-1 β converting enzyme like apoptosis protease-4, sometimes hereinafter referred to collectively as "ICE-LAP-3 and 4". The invention also relates to inhibiting the action of such polypeptides.

It has recently been discovered that an interleukin-1β converting enzyme (ICE) is responsible for cleaving pro-IL-1β into mature and active IL-1β and is also responsible for programmed cell death (or apoptosis), which is a process through which organisms get rid of unwanted cells. The present invention is directed to ICE-LAP-3 and 4 which are structurally related to ICE.

In the nematode caenorhabditis elegans, a genetic pathway of programmed cell death has been identified (Ellis, R. E., et al. Annu. Rev. Cell Biol., 7:663–698 (1991)). Two genes, ced-3 and ced-4, are essential for cells to undergo programmed cell death in *C. elegans* (Ellis, H. M., and Horvitz, H. R., Cell, 44:817–829 (1986)). Recessive mutations that eliminate the function of these two genes prevent normal programmed cell death during the development of *C. elegans*. The known vertebrate counterpart to ced-3 protein is ICE. The overall amino acid identity between ced-3 and ICE is 28%, with a region of 115 amino acids (residues 246–360 of ced-3 and 164–278 of ICE) that shows the highest identity (43%). This region contains a conserved pentapeptide, QACRG (residues 356–360 of ced-3), which contains a cysteine known to be essential for ICE function. The ICE-LAP-3 and 4 polypeptides of the present invention also have the same conserved pentapeptide and the cysteine residue which is essential for ICE function.

The similarity between ced-3 and ICE suggests not only that ced-3 might function as a cysteine protease but also that ICE might act as a vertebrate programmed cell death gene. ced-3 and the vertebrate counterpart, ICE, control programmed cell death during embryonic development, (Gagliarnini, V. et al., Science, 263:826:828 (1994).

ICE mRNA has been detected in a variety of tissues, including peripheral blood monocytes, peripheral blood lymphocytes, peripheral blood neutrophils, resting and activated peripheral blood T lymphocytes, placenta, the B lymphoblastoid line CB23, and monocytic leukemia cell line THP-1 cells (Cerretti, D. P., et al., Science, 256:97–100 (1992)), suggesting that ICE may have an additional substrate in addition to pro-IL-1β. The substrate that ICE acts upon to cause cell death is presently unknown. One possibility is that it may be a vertebrate homolog of the *C. elegans* cell death gene ced-4. Alternatively, ICE might directly cause cell death by proteolytically cleaving proteins that are essential for cell viability.

The mammalian gene bcl-2, has been found to protect immune cells called lymphocytes from cell suicide. Also, crmA, a cow pox virus gene protein product inhibits ICE's protein splitting activity.

The polypeptides of the present invention have been putatively identified as ICE-LAP-3 and 4. This identification has been made as a result of amino acid sequence homology.

In accordance with one aspect of the present invention, there are provided novel mature polypeptides which are ICE-LAP-3 and 4, as well as fragments, analogs and derivatives thereof. The polypeptides of the present invention are of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptides, or polynucleotides encoding such polypeptides for therapeutic purposes, for example, as an antiviral agent, an anti-tumor agent and to control embryonic development and tissue homeostasis.

In accordance with yet a further aspect of the present invention, there is provided an antibody against such polypeptides.

In accordance with yet another aspect of the present invention, there are provided antagonists to such polypeptides, which may be used to inhibit the action of such polypeptides, for example, in the treatment of Alzheimer's disease, Parkinson's disease, rheumatoid arthritis, septic shock and head injuries.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 shows the cDNA (SEQ ID NO:1) and corresponding deduced amino acid sequence (SEQ ID NO:2) of ICE-LAP-3 (SEQ ID NO:1). The polypeptide encoded by the amino acid sequence shown is the putative mature form of the polypeptide (minus the initial methionine residue), and the standard one-letter abbreviation for amino acids is used.

FIG. 2 shows the cDNA (SEQ ID NO:3) and corresponding deduced amino acid sequence of (SEQ ID NO:4) ICE-LAP-4 (SEQ ID NO:3). The polypeptide encoded by the amino acid sequence shown is the putative mature form of the polypeptide (minus the initial methionine residue).

Figure 3A:
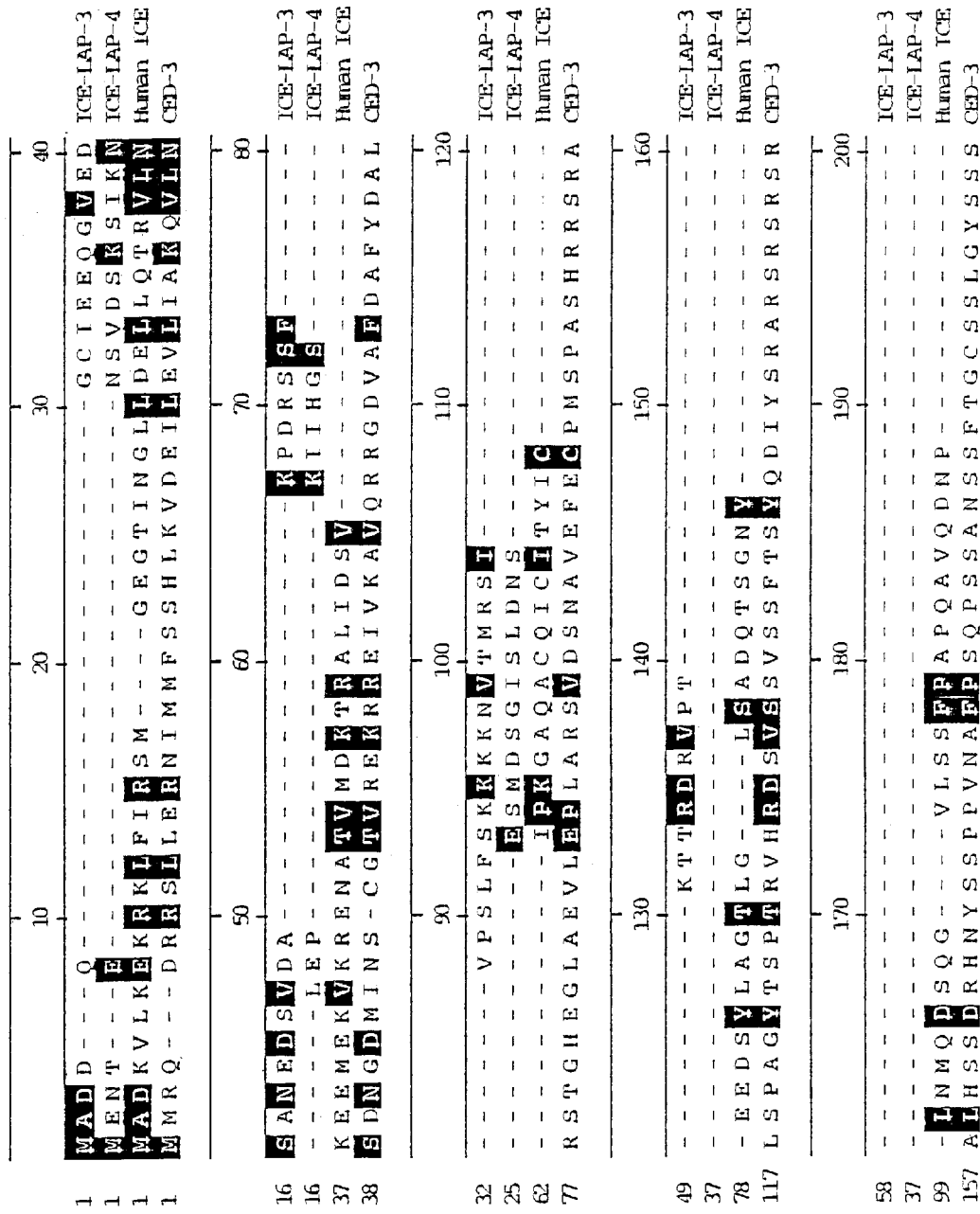
FIG. 3 shows an amino acid sequence comparison between ICE-LAP-3 (SEQ ID NO:2), ICE-LAP-4 (SEQ ID NO:4), human ICE and the *C. elegan* cell death gene ced-3. Shaded areas represent amino acid matches between the different sequences.
Figure 3C:
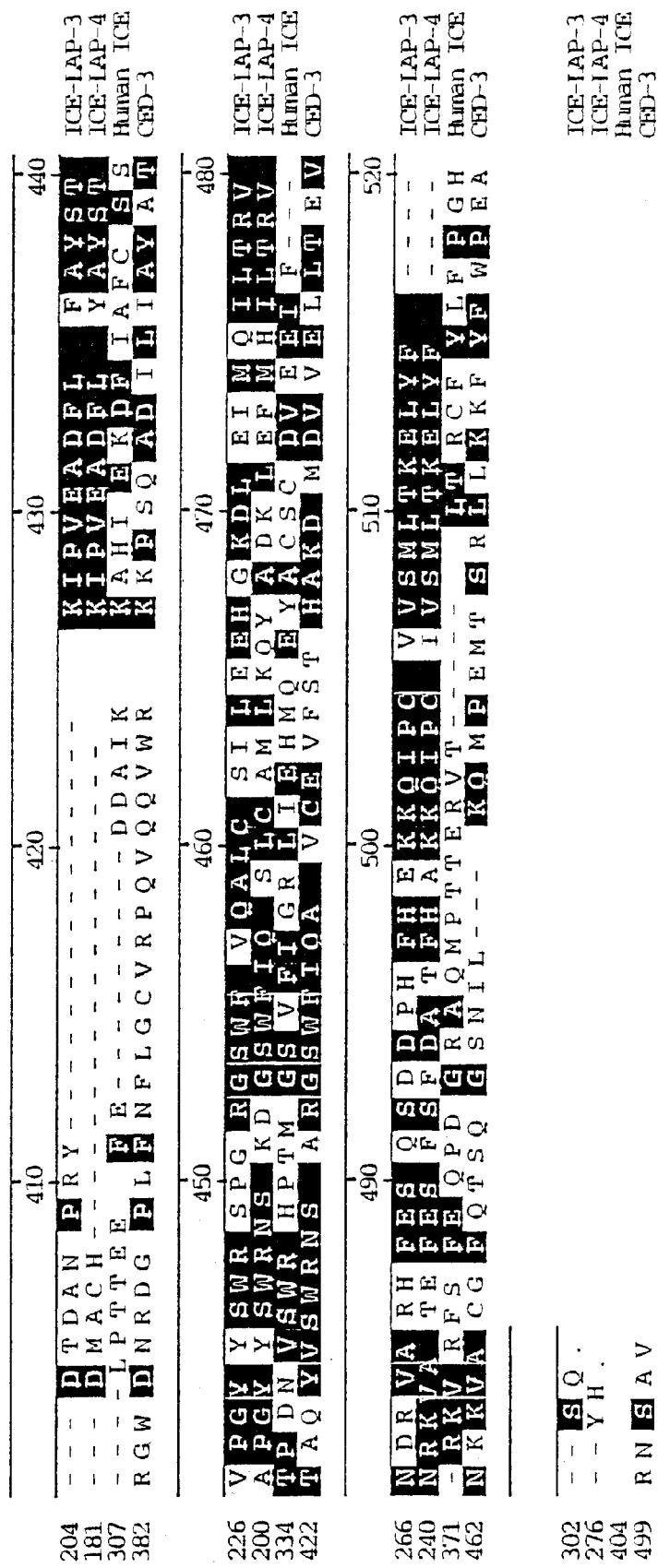

Sequencing inaccuracies are a common problem when attempting to determine polynucleotide sequences. Accordingly, the sequences of FIGS. 1 and 2 are based on several sequencing runs and the sequencing accuracy is considered to be at least 97%.

In accordance with an aspect of the present invention, there are provided isolated nucleic acids (polynucleotides) which encode the mature polypeptides having the deduced amino acid sequence of FIGS. 1 and 2 or for the mature polypeptide encoded by the cDNA of the clones deposited as ATCC Deposit No. 75875 encoding ICE-LAP-3 (SEQ ID NO:1), and ATCC Deposit No. 75873 encoding ICE-LAP-4 (SEQ ID NO:3), which were deposited Aug. 25, 1994.

These deposits are biological deposits with the ATCC, 12301 Parklawn Drive, Rockville, Md. 20852. Since the strains referred to are being maintained under the terms of the Budapest Treaty, they will be made available to a patent office signatory to the Budapest Treaty.

The polynucleotide encoding ICE-LAP-3 (SEQ ID NO:1) can be detected from human prostate, human endometrial tumor, human pancreatic tumor, human adrenal gland tumor and human tonsil. The full-length encoding ICE-LAP-3 was discovered in a cDNA library derived from human endometrial tumor. It is structurally related to the Interleukin-1β converting enzyme family. It contains an open reading frame encoding a protein of approximately 341 amino acid residues. The protein exhibits the highest degree of homology to *C. elegans* cell death gene ced-3 which is a homolog of human interleukin-1β converting enzyme, with 68% similarity and 43% identity over the entire amino acid sequence. It should be pointed out that the pentapeptide QACRG is conserved and is located at amino acid position 259–263.

The polynucleotide encoding ICE-LAP-4 (SEQ ID NO:3) was discovered in a cDNA library derived from human tonsils. It is structurally related to the ICE family. It contains an open reading frame encoding a protein of about 277 amino acid residues. The protein exhibits the highest degree of homology to the *C. elegans* cell death gene ced-3 with 29% identity and 46% similarity over a 277 amino acid stretch. It is also important that the pentapeptide QACRG is conserved and is located at amino position 161–165.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encode the mature polypeptides may be identical to the coding sequence shown in FIGS. 1 and 2 or that of the deposited clones or may be a different coding sequence which coding sequence, as a result of the redundancy or degeneracy of the genetic code, encode the same mature polypeptides, and derivatives thereof, as the DNA of FIGS. 1 and 2 or the deposited cDNA.

The polynucleotides which encode for the mature polypeptides of FIGS. 1 and 2 or for the mature polypeptides encoded by the deposited cDNAs may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptides having the deduced amino acid sequence of FIGS. 1 and 2 or the polypeptides encoded by the cDNA of the deposited clones. The variants of the polynucleotides may be naturally occurring allelic variants of the polynucleotides or non-naturally occurring variants of the polynucleotides.

Thus, the present invention includes polynucleotides encoding the same mature polypeptides as shown in FIGS. 1 and 2 or the same mature polypeptides encoded by the cDNA of the deposited clones as well as variants of such polynucleotides which variants encode for a fragment, derivative or analog of the polypeptides of FIGS. 1 and 2 or the polypeptides encoded by the cDNA of the deposited clones. Such nucleotide variants include deletion variants, substitution variants and addition or insertion variants.

As hereinabove indicated, the polynucleotides may have a coding sequence which is a naturally occurring allelic variant of the coding sequence shown in FIGS. 1 and 2 or of the coding sequence of the deposited clones. As known in the art, an allelic variant is an alternate form of a polynucleotide sequence which may have a substitution, deletion or addition of nucleotides, which does not substantially alter the function of the encoded polypeptides.

The polynucleotides of the present invention may also have the coding sequence fused in frame to a sequence which allows for purification of the polypeptide of the present invention. The marker sequence may be a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptides encoded by the cDNA of FIGS. 1 and 2 or the deposited cDNAs.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to ICE-LAP-3 and 4 (SEQ ID NOS:2 and 4) polypeptides which have the deduced amino acid sequence of FIGS. 1 and 2 or which has the amino acid sequence encoded by the deposited cDNAs, as well as fragments, analogs and derivatives of such polypeptides.

The terms "fragment," "derivative" and "analog" when referring to the polypeptides of FIGS. 1 and 2 or that encoded by the deposited cDNA, means polypeptides which retain essentially the same biological function or activity as such polypeptides, and wherein derivatives include polypeptides with enhanced or reduced biological function. An analog includes a proprotein which can be activated by cleavage of the proprotein portion to produce active mature polypeptides.

The polypeptides of the present invention may be recombinant polypeptides, natural polypeptides or synthetic polypeptides, preferably recombinant polypeptides.

The fragment, derivative or analog of the polypeptides of FIGS. 1 and 2 or that encoded by the deposited cDNAs may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol). Such fragments, derivatives and analogs are deemed to be within the scope of those skilled in the art from the teachings herein.

The polypeptides and polynucleotides of the present invention are preferably provided in an isolated form, and preferably are purified to homogeneity. The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the ICE-LAP-3 and 4 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTRs from retroviruses, e.g. RSV, HIV, HTLVI, CMV or SV40 promoter, the *E. coli.* lac or trp, the phage lambda $P_L$ promoter and other promoters known to control expression of genes in prokaryotic or eukaryotic cells or their viruses. However, also cellular signals can be used, for example, human-β-actin-promoter). The expression vector can contain a ribosome binding site for translation initiation and a transcription terminator. The vector may also include appropriate sequences for amplifying the copy number of the gene.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Bacillus subtilis,* Streptomyces, *Salmonella typhimurium;* fungal cells, such as yeast; insect cells such as Drosophila and Sf9; animal cells such as CHO, COS, HEK 293 or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, PSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, lipofection or electroporation.

(Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include $E.$ $coli,$ $Bacillus$ $subtilis,$ $Salmonella$ $typhimurium$ and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors may comprise an origin of replication, a suitable promoter and enhancer, polyadenylation site, splice donor and acceptor sites, transcriptional termination sequences, and 5' flanking nontranscribed sequences. DNA sequences derived from the SV40 splice and polyadenylation sites may be used to provide the required nontranscribed genetic elements.

The ICE-LAP-3 and 4 polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The ICE-LAP-3 and 4 polypeptides may be employed to treat abnormally controlled programmed cell death. Abnormally controlled programmed cell death may be an underlying cause of cancers due to an abnormal amount of cell growth. Accordingly, since ICE-LAP genes are implicated in programmed cell death, they may be used to target unwanted cells, for example, cancerous cells. ICE-LAP-3 and 4 may also be used to control vertebrate development and tissue homeostasis, due to its apoptosis ability.

Also, ICE-LAP-3 and 4 polypeptides may be used to overcome many viral infections by overcoming the suppressed programmed cell death, since programmed cell death may be one of the primary antiviral defense mechanisms of cells.

ICE-LAP-3 and 4 may also be employed to treat immunosuppression related disorders, such as AIDS, by targeting virus infected cells for cell death.

This invention also provides the use of the human ICE-LAP-3 and 4 genes as a diagnostic. For example, some diseases result from inherited defective genes. These genes can be detected by comparing the sequence of the defective gene with that of a normal one. That is, a mutant gene would be associated with abnormal cell growth, for example cancer, or a susceptibility to abnormal cell growth.

Individuals carrying mutations in the human ICE-LAP-3 and 4 genes may be detected at the DNA level by a variety of techniques. Nucleic acids used for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986) prior to analysis. RNA or cDNA may also be used for the same purpose. Deletions or insertions can be detected by a change in size of the amplified product in comparison to the normal genotype. Point mutations can be identified by hybridizing amplified DNA to radiolabeled ICE-LAP-3 and 4 RNA or alternatively, radiolabeled ICE-LAP-3 and 4 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing fornamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase protection and S1 protection or the chemical cleavage method (e.g., Cotton et al., PNAS, USA, 85:4397–4401 (1985)).

Thus, the detection of a specific DNA sequence may be achieved by method such as hybridization, RNase protection, chemical cleavage, direct DNA sequencing, or the use of restriction enzymes, e.g., restriction fragment length polymorphisms, and Southern blotting of genomic DNA. Also, mutations may be detected by in situ analysis.

In addition, some diseases are a result of, or are characterized by, changes in gene expression which can be detected by changes in the mRNA. Alternatively, the ICE-LAP-3 and 4 genes can be used as a reference to identify individuals expressing a decreased level of ICE-LAP-3 and 4 protein, e.g., by Northern blotting.

The present invention also relates to a diagnostic assay for detecting levels of ICE-LAP-3 and 4 protein in a sample taken from a host, for example, a blood, urine or serum sample. An altered level of the ICE-LAP polypeptides is indicative of a cancer or immunodeficiency diagnosis. The level of ICE-LAP-3 and 4 may be detected, for example, by an immunoassay technique by procedures which are apparent to those of skill in the art from the teachings herein. An example of such an assay is a sandwich assay which utilizes two antibodies specific to an ICE-LAP-3 or 4 antigen, preferably monoclonal antibodies with one of the antibodies being labeled, eg. by coupling a suitable label such as an indicator enzyme, eg. horseradish peroxidase. The unlabeled antibody is preferably on a solid support. If antigen is present, the antigen will bind to both antibodies. After binding of the peroxidase-coupled antibody to the antigen, the peroxidase can be used to generate a colored product that is measurable and whose concentration is related to the amount of antigen in a sample. Because of the catalytic nature of the enzyme the system greatly amplifies the signal. Altered levels of ICE-LAP-3 and 4 are indicative of the particular diseases mentioned above. Also, an ELISA assay may be employed to detect the amount of ICE-LAP-3 and 4 in a sample.

The polypeptides of the present invention may also be used for identifying other molecules which have similar biological activity. An example of a screen for this comprises isolating the coding region of the ICE-LAP genes by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention is further related to a process of screening molecules to identify antagonists or agonists of the ICE-LAP-3 and 4 polypeptides of the present invention. Agonists increase the natural biological function of ICE-LAP-3 and 4, while antagonists reduce or eliminate such function. An example of such an assay comprises combining ICE-LAP-3 and 4 and a potential antagonist or agonist compound with their natural substrate under conditions allowing for action upon the substrate and determining whether the compound prevents ICE-LAP-3 or 4 from cleaving the substrate or enhances the cleavage.

Potential antagonists include an antibody, or in some cases, an oligonucleotide, which binds to the polypeptide. Alternatively, a potential antagonist may be a closely related protein which binds to the substrate, however, they are inactive forms of the polypeptide and thereby prevent the action of ICE-LAP-3 and 4.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of ICE-LAP-3 and 4. The antisense RNA oligonucleotide hybridizes to the mRNA in vivo and blocks translation of the mRNA molecule into the polypeptides (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of ICE-LAP-3 and 4.

Potential antagonists include a small molecule which binds to and occupies the catalytic site of the polypeptide thereby making the catalytic site inaccessible to substrate such that normal biological activity is prevented. Examples of small molecules include but are not limited to small peptides or peptide-like molecules.

The antagonists may be employed to treat non-programmed necrotic cell death related to cardiovascular diseases, strokes, trauma, and other degenerative diseases where abnormal regulation of ICE-LAP-3 and 4 may lead to pathological cell death, for example, immunosuppression-related disorders, Alzheimer's disease, Parkinson's disease, rheumatoid arthritis.

The antagonists may also be used to treat immune-based diseases of the lung and airways, central nervous system, eyes and ears, joints, bones, cardiovascular system and gastrointestinal and urogenital systems The antagonists may be employed in a composition with a pharmaceutically acceptable carrier, e.g., as hereinafter described.

The polypeptides and antagonists and agonists of the present invention may be employed in combination with a suitable pharmaceutical carrier. Such compositions comprise a therapeutically effective amount of the polypeptide or antagonist or agonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the intravenous, intraperitoneal, intramuscular, subcutaneous, intranasal or intradermal routes. The pharmaceutical compositions are administered in an amount which is effective for treating and/or prophylaxis of the specific indication. In general, they will be administered in an amount of at least 10 $\mu$g/kg body weight, and in most cases they will be administered in an amount not in excess of 8 mg/Kg body weight per day. In most cases, the dosage is from about 10 $\mu$g/kg to about 1 mg/kg body weight daily, taking into account the routes of administration, symptoms, etc.

The ICE-LAP-3 and 4 polypeptides, and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cCDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes (this assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980), or agarose gels (0.5–1.5%).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1
Bacterial Expression and Purification of ICE-LAP-3

The DNA sequence encoding ICE-LAP-3, ATCC #75875, is initially amplified using PCR oligonucleotide primers corresponding to the 5' sequences of the processed ICE-LAP-3 protein (minus the signal peptide sequence) and the vector sequences 3' to the ICE-LAP-3 gene. Additional nucleotides corresponding to ICE-LAP-3 are added to the 5' and 3' sequences respectively. The 5' oligonucleotide primer has the sequence 5' GATC GGATCCATGCGTGCGGGGACACGGGTC 3' contains a Bam HI restriction enzyme site (underlined) followed by 18 nucleotides of ICE-LAP-3 coding sequence starting from the presumed terminal amino acid of the processed protein codon. The 3' sequence 5' GTAC TCTAGATCATTCACCCTGGTGGAGGAT 3' contains complementary sequences to an Xba I site (underlined) followed by 21 nucleotides of ICE-LAP-3. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with Bam HI and Xba I. The amplified sequences are ligated into pQE-9 and are inserted in frame with the sequence encoding for the histidine tag and the RBS. The ligation mixture is then used to transform E. coli available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized ICE-LAP-3 is purified from this solution by chromatography on a Nickel-Chelate column under conditions that allow for tight binding by proteins containing the 6-His tag (Hochuli, E. et al., J. Chromatography 411:177–184 (1984)). ICE-LAP-3 (95% pure is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2
Bacterial Expression and Purification of ICE-LAP-4

The DNA sequence encoding ICE-LAP-4, ATCC #75873, is initially amplified using PCR oligonucleotide primers corresponding to the 5' sequences of the processed ICE-LAP-4 protein (minus the signal peptide sequence) and the vector sequences 3' to the ICE-LAP-4 gene. Additional nucleotides corresponding to ICE-LAP-4 are added to the 5' and 3' sequences respectively. The 5' oligonucleotide primer has the sequence 5' GATC GGATCCATGGAGAACACTGAAAACTCA 3' (SEQ ID NO:5) contains a Bam HI restriction enzyme site (underlined) followed by 18 nucleotides of ICE-LAP-4 coding sequence starting from the presumed terminal amino acid of the processed protein codon. The 3' sequence 5' GTACTCTAGATTAGTGATAAAAATAGAGTTC 3' (SEQ ID NO:6) contains complementary sequences to an Xba I site (underlined) followed by 21 nucleotides of ICE-LAP-4. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with Bam HI and Xba I. The amplified sequences are ligated into pQE-9 and are inserted in frame with the sequence encoding for the histidine tag and the RBS. The ligation mixture is then used to transform E. coli available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 nM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized ICE-LAP-4 is purified from this solution by chromatography on a Nickel-Chelate column under conditions that allow for tight binding by proteins containing the 6-His tag (Hochuli, E. et al., J. Chromatography 411:177–184 (1984)). ICE-LAP-4 (95% pure is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 3
Expression of Recombinant ICE-LAP-3 in COS Cells

The expression of a plasmid, ICE-LAP-3 HA, is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire ICE-LAP-3 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding for ICE-LAP-3, ATCC #75875, was constructed by PCR on the full-length ICE-LAP-3 using two primers: the 5' primer 5' GACTATGCGT-GCGGGGACACGG 3' (SEQ ID NO:7) contains the ICE-LAP-3 translational initiation site ATG followed by 5 nucleotides of ICE-LAP-3 coding sequence starting from the initiation codon; the 3' sequence 5' AATCAAGCGTAG TCTGGGACGTCGTATGGGTATTCAC-CCTGGTGGAGGATTTG 3 ' (SEQ ID NO:9) contains translation stop codon, HA tag and the last 21 nucleotides of the ICE-LAP-3 coding sequence (not including the stop codon). Therefore, the PCR product contains the ICE-LAP-3 coding sequence followed by HA tag fused in frame, and a translation termination stop codon next to the HA tag. The PCR amplified DNA fragment was ligated with pcDNAI/Amp by blunt end ligation. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant ICE-LAP-3, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the ICE-LAP-3 HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 4
Expression of Recombinant ICE-LAP-4 in COS Cells

The expression of a plasmid, ICE-LAP-4 HA, is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire ICE-LAP-4 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows: The DNA sequence encoding for ICE-LAP-4, ATCC #75873, was constructed by PCR on the full-length ICE-LAP-4 using two primers: the 5' primer 5' ACCATG-GAGAACACTGAAAAC 3' (SEQ ID NO:9) contains the ICE-LAP-4 translational initiation site, ATG, followed by 15 nucleotides of ICE-LAP-4 coding sequence starting from the initiation codon; the 3' sequence 5' AATCAAGCG-TAGTCTGGGACGTCGTATGGGTAGT-GATAAAAATAGAGTTCTTT 3' (SEQ ID NO:10) contains translation stop codon, HA tag and the last 21 nucleotides of the ICE-LAP-4 coding sequence (not including the stop codon). Therefore, the PCR product contains the ICE-LAP-4 coding sequence followed by HA tag fused in frame, and a translation termination stop codon next to the HA tag. The PCR amplified DNA fragment was ligated with pcDNAI/Amp by blunt end ligation. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant ICE-LAP-4, COS cells were transfected with the expression vector by the DEAE-DEXTRAN method (J. Sambrook, E. Fritsch, T. Maniatis, Molecular Cloning: A Laboratory Manual, Cold Spring Laboratory Press, (1989)). The expression of the ICE-LAP-4 HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 5
Expression Pattern of ICE-LAP-3 in Human Tissue

Northern blot analysis was carried out to examine the levels of expression of ICE-LAP-3 in human tissues. Total cellular RNA samples were isolated with RNAzol™ B system (Biotecx Laboratories, Inc. 6023 South Loop East, Houston, Tex. 77033). About 10 µg of total RNA isolated from each human tissue specified was separated on 1% agarose gel and blotted onto a nylon filter (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime-3 Prime, Inc. 5603 Arapahoe Road, Boulder, Colo. 80303). The filter was then hybridized with radioactive labeled full length ICE-LAP-3 gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. The message RNA for ICE-LAP-3 is abundant in liver.

EXAMPLE 6
Expression Pattern of ICE-LAP-4 in Human Tissue

Northern blot analysis is carried out to examine the levels of expression of ICE-LAP-4 in human tissues. Total cellular RNA samples were isolated with RNAzol™ B system (Biotecx Laboratories, Inc. 6023 South Loop East, Houston, Tex. 77033). About 10 µg of total RNA isolated from each human tissue specified was separated on 1% agarose gel and blotted onto a nylon filter (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime-3 Prime, Inc. 5603 Arapahoe Road, Boulder, Colo. 80303). The filter was then hybridized with radioactive labeled full length ICE-LAP-4 gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen.

Numerous modifications and variations of the present invention are possible in light of the above teachings and, therefore, within the scope of the appended claims, the invention may be practiced otherwise than as particularly described.

What is claimed is:

1. A purified protein comprising an amino acid sequence selected from the group consisting of:

(a) the amino acid sequence shown as SEQ ID NO:4;
    (b) the amino acid sequence shown as SEQ ID NO:4, but lacking the N-terminal methionine residue; and
    (c) the amino acid sequence of a fragment of the polypeptide shown as residues 2 to 277 in SEQ ID NO:4 wherein said polypeptide fragment has apoptosis inducing activity.

2. The purified protein of claim 1, which comprises the amino acid sequence shown as SEQ ID NO:4.

3. The purified protein of claim 1, which comprises the amino acid sequence shown as SEQ ID NO:4, but lacking the N-terminal methionine residue.

4. The purified protein of claim 1, which comprises the amino acid sequence of a fragment of the polypeptide shown as residues 2 to 277 in SEQ ID NO:4, wherein said polypeptide fragment has apoptosis inducing activity.

5. The purified protein of claim 1, which comprises a heterologous polypeptide sequence.

6. A composition comprising the purified protein of claim 1 and a pharmaceutically acceptable carrier.

7. A purified protein comprising an amino acid sequence encoded by a polynucleotide sequence capable of hybridizing to the complement of a polynucleotide consisting of SEQ ID NO:3 when incubated together in 0.5 M NaPO$_4$, pH 7.4 and 7% SDS overnight at 65° C. followed by washing twice at room temperature and twice at 60° C. with 0.5× SSC, and 0.1% SDS, wherein a polypeptide consisting of such amino acid sequence has apoptosis inducing activity.

8. The purified protein of claim 7, which comprises a heterologous polypeptide sequence.

9. A composition comprising the purified protein of claim 7 and a pharmaceutically acceptable carrier.

10. A purified protein comprising an amino acid sequence selected from the group consisting of:
  (a) the amino acid sequence of the polypeptide encoded by the cDNA contained in ATCC Deposit No. 75873,
  (b) the amino acid sequence of the polypeptide encoded by the cDNA contained in ATCC Deposit No. 75873, but lacking the N-terminal methionine residue; and
  (c) the amino acid sequence of a fragment of the polypeptide encoded by the cDNA contained in ATCC Deposit No. 75873, wherein said polypeptide fragment has apoptosis inducing activity.

11. The purified protein of claim 10, which comprises the amino acid sequence of the polypeptide encoded by the cDNA contained in ATCC Deposit No. 75873.

12. The purified protein of claim 10, which comprises the amino acid sequence of the polypeptide encoded by the cDNA contained in ATCC Deposit No. 75873, but lacking the N-terminal methionine residue.

13. The purified protein of claim 10, which comprises the amino acid sequence of a fragment of the polypeptide encoded by the cDNA contained in ATCC Deposit No. 75873, wherein said polypeptide fragment has apoptosis inducing activity.

14. The purified protein of claim 10, which comprises a heterologous polypeptide sequence.

15. A composition comprising the purified protein of claim 10 and a pharmaceutically acceptable carrier.

* * * * *